United States Patent [19]

Miwa et al.

[11] Patent Number: 5,034,318
[45] Date of Patent: Jul. 23, 1991

[54] METHOD FOR PRODUCING L-TRYPTOPHAN BY FERMENTATION

[75] Inventors: Kiyoshi Miwa, Matsudo; Shigeru Nakamori, Yokohama; Konosuke Sano, Tokyo, all of Japan

[73] Assignee: Ajinomoto Co., Inc., Tokyo, Japan

[21] Appl. No.: 501,329

[22] Filed: Mar. 22, 1990

Related U.S. Application Data

[63] Continuation of Ser. No. 948,396, Dec. 30, 1986, abandoned, which is a continuation of Ser. No. 602,330, Apr. 20, 1984, abandoned.

[30] Foreign Application Priority Data

Apr. 23, 1983 [JP] Japan ................................. 58-71945

[51] Int. Cl.⁵ .......................... C12P 13/22; C12N 1/21
[52] U.S. Cl. ............................... 435/108; 435/252.32;
435/320.1; 435/840; 435/843; 935/29; 935/60; 935/72
[58] Field of Search ........................... 435/108, 252.32

[56] References Cited

FOREIGN PATENT DOCUMENTS 0058889 9/1982 European Pat. Off. ............ 435/843
0124048 11/1984 European Pat. Off. ................ 935/9
2098603 11/1982 United Kingdom ................ 435/108

OTHER PUBLICATIONS

Aiba, et al., *Applied & Environmental Microbiology*, vol. 43(2), pp. 289–297, 1982.

*Primary Examiner*—Richard A. Schwartz
*Assistant Examiner*—John L. LeGuyader
*Attorney, Agent, or Firm*—Oblon, Spivak, McClelland, Maier & Neustadt

[57] ABSTRACT

A method for producing L-tryptophan comprising culturing coryneform glutamic acid-producing bacteria transformed with an expression vector capable of replicating and expressing an operably linked anthranilic acid phosphoribosyl transferase gene isolated from a brevibacterium glutamic acid-producing bacterium, growing the transformants in culture medium allowing for the production of L-tryptophan and recovering the L-tryptophan accumulated in the culture medium.

5 Claims, 4 Drawing Sheets

METHOD FOR PRODUCING L-TRYPTOPHAN BY FERMENTATION

This application is a continuation of application Ser. No. 06/948,396, filed on Dec. 30, 1986, now abandoned, which is a continuation of Ser. No. 06/602,330, filed Apr. 20, 1984, now abandoned.

BACKGROUND OF THE INVENTION

1. Field of the Invention

The present invention relates to a method for producing L-tryptophan by fermentation, and particularly relates to a method for producing L-tryptophan by fermentation using Coryneform glutamic acid-producing bacteria constructed by a gene-recombination technique.

2. Description of the Prior Art

When L-tryptophan is to be produced by fermentation, artificial mutation has been given to wild strains to impart L-tryptophan productivity to them because wild strains hardly produce L-tryptophan outside their cells.

As previously known artificial mutants having L-tryptophan productivity, there can be cited mutants of the genus of Brevibacterium, Microbacterium or Corynebacterium that are resistant to 5-methyltryptophan mutants of the genus Corynebacterium that require tyrosine and phenylalanine for growth and are resistant to phenylalanine antagonists (Japanese Patent Publication No. 19037/1976), mutants of the genus of Bacillus that are resistant to 5-fluorotryptophan (Japanese Patent Laid-Open No. 85289/1974) and mutants of the genus of Brevibacterium that are resistant to 5-methyltryptophan and to m-fluorotryptophan (Japanese Patent Laid-Open No. 42091/1975).

On the other hand, recently some reports have been made on trials of construction of L-tryptophan-producing bacteria using a gene recombination technique different from the above-mentioned artificial mutation technique. For example, it was reported in Appl. Environ. Microbiol. 38, (2), 181-190 (1979) that the specific mutants of *Escherichia coli* that contained a plasmid having trp E 472 genes of *Escherichia coli* produced about 1.3 g/l of L-tryptophan. In addition, it was also mentioned in Proceedings of 1980 Annual Meeting of the Society of Fermentation Technology, Japan, page 170 that mutants of *Escherichia coli* containing a plasmid having the tryptophan operons of *Escherichia coli* produced 360 mg/l of L-tryptophan.

Although several high tryptophan-producers have been known among the mutants of Coryneform glutamic acid-producing bacteria as mentioned above, there has been no significant trial so far as the inventors know to construct tryptophan-producer using such Coryneform-bacteria as above which have high potential ability to produce L-tryptophan.

A need, therefore, continues to exist for a more efficient method for producing L-tryptophan by fermentation.

SUMMARY OF THE INVENTION

It is therefore an object of the present invention to provide a novel method for producing L-tryptophan by fermentation using Coryneform bacteria constructed by a gene-recombination technique.

This and other objects of the invention, as will hereinafter become more readily apparent, have been attained by providing:

A method for producing L-tryptophan characterized by culturing a microorganism capable of producing L-tryptophan and then recovering the L-tryptophan accumulated in the culture liquid, which microorganism has been obtained by ligating a gene with a vector plasmid capable of self-replicating in cells of Coryneform glutamic acid-producing bacteria and then incorporating the recombinant plasmid into a DNA-recipient belonging to Coryneform glutamic acid-producing bacteria, the gene having been obtained from a DNA-donor belonging to Coryneform glutamic acid-producing bacteria and, when the gene is ligated with a vector plasmid capable of self-replicating in cells of Coryneform glutamic acid-producing bacteria and then the recombinant plasmid is incorporated into a mutant derived from Coryneform glutamic acid-producing bacteria and requiring at least L-tryptophan for growth, being able to eliminate the requirement for L-tryptophan of the mutant

BRIEF DESCRIPTION OF THE INVENTION

DESCRIPTION OF THE PREFERRED EMBODIMENTS

Figure 1:
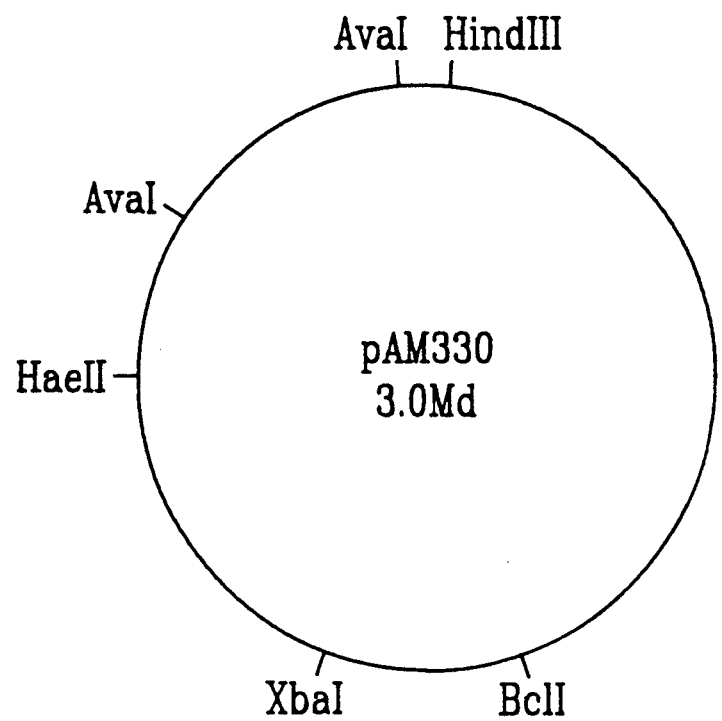
FIG. 1 shows a restriction map of plasmid pAM 330.

The recombinant plasmid in the method of the present invention at least possesses a DNA fragment which contains a gene that, when incorporated into mutants derived from Coryneform glutamic acid-producing bacteria and requiring at least L-tryptophan, can eliminate the requirement for L-tryptophan of the mutants and are termed tryptophan biosynthesis genes hereinafter.

The DNA fragments containing the tryptophan biosynthesis genes can be obtained from the chromosome DNA of Coryneform glutamic acid-producing bacteria. (Bacteria that provide DNA fragments containing tryptophan biosynthesis genes are termed DNA-donors.)

Coryneform bacteria are aerobic, gram-positive rods, and non-acidfast and are described in Bergey's Manual of Determinative Bacteriology, 8th edition, 599, (1974). As examples of specimens of wild strains of Coryneform glutamic acid-producing bacteria of the present invention, the following can be cited:

| | |
|---|---|
| *Brevibacterium divaricatum* | ATCC 14020 |
| *Brevibacterium saccharolyticm* | ATCC 14066 |
| *Brevibacterium immaliophilum* | ATCC 14068 |
| *Brevibacterium lactofermentum* | ATCC 13869 |
| *Brevibacterium roseum* | ATCC 13825 |
| *Brevibacterium flavum* | ATCC 19240 |
| *Corynebacterium acetoacidfilum* | ATCC 15806 |
| *Corynebacterium callunae* | ATCC 15991 |
| *Corynebacterium glutamium* | ATCC 13032, 13060 |
| *Corynebacterium lilium* | ATCC 15990 |
| *Corynebacterium melassecola* | ATCC 17965 |

| | |
|---|---|
| *Microbacterium ammoniaphilum* | ATCC 15354 |

Coryneform glutamic acid-producing bacteria of the present invention include also mutants of the wild strains of Coryneform glutamic acid-producing bacteria having lost productivity of glutamic acid and various mutants producing amino acids such as lysine and arginine, purine nucleosides such as inosine, purine nucleotides such as inosine-5'-monophosphate or other products.

It is preferable to use mutants having biosynthetic activity for tryptophan or its precursor elevated due to mutation such as resistance to tryptophan antagonists imparted to them, as DNA-donors.

As examples of tryptophan antagonists, there can be cited 4-fluorotryptophan (abbreviated as 4-FT hereinafter), 5-fluorotryptophan (abbreviated as 5-FT hereinafter), 6-fluorotryptophan, 7-fluorotryptophan, 4-methyltryptophan, 5-methyltryptophan, 6-methyltryptophan, 7-methyltryptophan, naphthylalanine, indoleacrylic acid, naphthylacrylic acid, β-(2-benzothienyl)-alanine, styrylacetic acid, indole and tryptozan. Precursors of tryptophan mean 3-dehydroxy-D-arabino-hepturonic acid-7-phosphate, 3-dehydroquinic acid, 3-dehydroshikimic acid, shikimic acid, shikimic acid-3-phosphate, 5-enolpyruvylshikimic acid-3-phosphate, chorismic acid, anthranilic acid, N-o-carboxyphenyl-D-ribosylamine-5'-phosphate, 1-(o-carboxyphenyl-amino)-1-deoxyribulose-5'-phosphate, and indole-3-glycerol phosphate.

As examples of the mutants, there can be cited mutants of the genus of Brevibacterium, Microbacterium or Corynebacterium that are resistant to 5-methyltryptophan (U.S. Pat. No. 3,700,539), mutants of the genus Brevibacterium that are resistant to 5-methyltryptophan and to m-fluorotryptophan (Japanese Patent Laid-Open No. 42091/1975) and the like.

As an example of the mutants having an elevated biosynthetic activity for precursors of tryptophan, a strain having an elevated biosynthetic activity for anthranilic acid due to elimination of a feedback inhibition by tryptophan is described in Agric Biol. Chem., 39, 627, (1975).

As the DNA-donors, strains other than Coryneform glutamic acid-producing bacteria, for example, *Escherichia coli* and the like can also be used.

As the tryptophan biosynthesis genes, there can be cited genes for 3-deoxy-D-arabino-hepturonic acid-7-phosphate (DAHP) synthetase, 3-dehydroquinic acid synthetase, 3-dehydroquinic acid dehydratase, shikimic acid dehydrogenase, shikimic acid kinase, 5-enolpyruvyl-shikimic acid-3-phosphate synthetase, chorismic acid synthetase, anthranilic acid synthetase, anthranilic acid phosphoribosyl transferase, N-(5'-phosphoribosyl)-anthranilic acid isomerse, indole-3-glycerol phosphoric acid synthetase, and tryptophan synthetase. When these genes are inserted into the vector plasmid capable of self-replicating in the host cells and then the recombinant plasmid is incorporated into DNA-recipients belonging to Coryneform glutamic acid-producing bacteria, strains having an elevated productivity for tryptophan can be obtained.

As the tryptophan biosynthesis genes, the above-mentioned wild type ones are used also, and additionally mutated genes derived by mutation to give properties such as resistance to tryptophan antagonists as mentioned above are preferably used. Such mutation of genes can be carried out, after obtaining the wild type genes incorporated into host cells, the host cells are subjected to mutation. Wild type genes can be mutated also to expose separated recombinant DNA having the wild type gene therein in vitro. The improvement of the genes by mutation means the modification of the genes for providing desirable effects of accelerating the production of tryptophan by an increase in the synthetic amount of tryptophan biosynthesis enzymes that are products of the genes and an increase in the specific activity per molecule of the enzymes and by the reduction or elimination of enzymatic inhibition made by intermediate products of tryptophan biosynthesis and the final product. To be concrete, the improvement of the genes can be achieved by the mutation or change of promotor region or the mutation and modification of structural genes.

After inserting a plurality of tryptophan biosynthesis genes into the same plasmid or after separately inserting a plurality of the genes into a plurality of coexisting vector plasmids, these plasmids are incorporated into DNA-recipients. In such cases, better results may be obtained.

As the DNA-recipients belonging to Coryneform glutamic acid-producing bacteria, various strains can be used. When strains requiring tryptophan for growth are used as the recipients, strains transformed with tryptophan biosynthesis genes can be easily selected due to disappearance of the requirement for tryptophan. When strains sensitive to tryptophan antagonists are used as the DNA-recipients and tryptophan biosynthesis genes having resistance to tryptophan antagonists are incorporated into the recipients, the transformed strains can be easily selected as strains which become resistant to the tryptophan antagonists. To obtain transformed strains having an improved ability to produce tryptophan, it is preferable to use as the recipients mutants having an increased biosynthetic activity for tryptophan or its precursor due to mutations such as resistance to tryptophan antagonists and nutrition requirement. Mutants having the improved permeability of tryptophan, mutants having lowered decomposition activity of tryptophan and mutants or strains having recombinant genes which have elevated biosynthetic abilities for metabolic products such as serine, glutamine and pyruvic acid that supply tryptophan biosynthesis with raw materials may bring good results, when used as the recipient.

As the vector of the present invention, any plasmids capable of self-replicating in Coryneform glutamic acid-producing bacteria may be used.

As specimens of the vectors, the following can be cited.

(1) pAM 330
(a) Separation source: *Brevibacterium lactofermentum* ATCC 13869
(b) Molecular weight: 3.0 mega dalton (calculated from a migration distance on agarose gel electrophoresis and the chain length of DNA under an electron microscope)
(c) Cleavage sites with restriction enzymes: Shown in Table 1.
(d) Map of cleavage sites with restriction enzymes: Refer to FIG. 1.
(e) Other properties: Cryptic plasmid

TABLE 1

Figure 2:
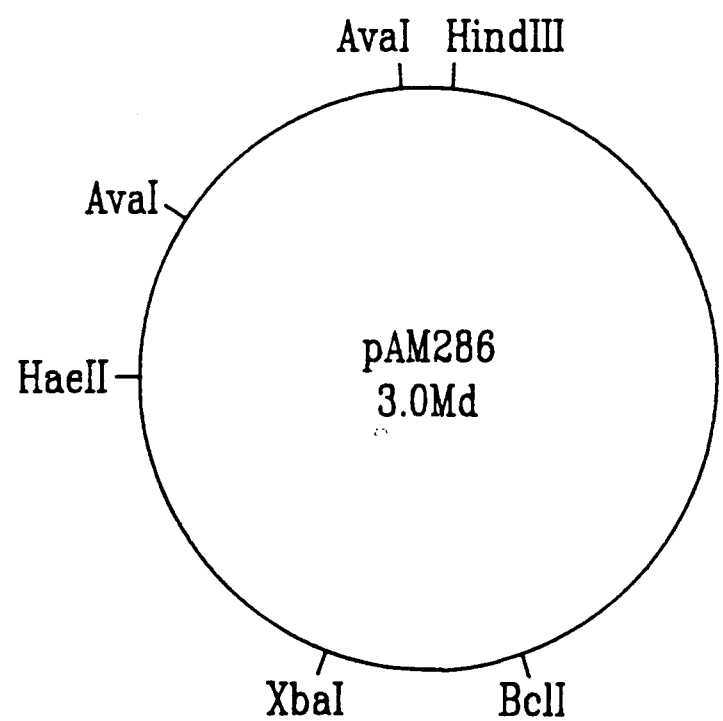
FIG. 2 shows a restriction map of plasmid pAM 286.

| Restriction enzyme | Number of restriction Site |
| --- | --- |
| Alu I *Arthrobacter lutus* | ≧4 |
| Ava I *Anabena variabilis* | ≧2 |
| Bcl I *Bacillus caldolyticus* | 1 |
| BamH I *Bacillus amyroliquefaciens* H | 0 |
| Bgl II *Bacillus globigii* | 0 |
| BstE II *Bacillus stearothermophilus* ET | ≧4 |
| EcoR I *Escherichia coli* RI+ | 0 |
| Hae II *Haemophilus eagyptius* | 1 |
| HgiA I *Herpetosiphon gyganteus* | ≧4 |
| Hind II *Hemophilus influenzae* | ≧4 |
| Hind III *Hemophilus influenzae* | 1 |
| Hpa II *Hemophilus parainfluenzae* | ≧4 |
| Kpn I *Klebsiella pneumoniae* | 0 |
| Pvu II *Proteus vulgaris* | 0 |
| Sac I *Streptomyces achromogenes* | 0 |
| Sal I *Streptomyces albus* | 0 |
| Sau 3a *Staphylococcus aureus* | ≧4 |
| Sma I *Seratia marcescens* | 1 |
| Sst I *Streptomyces stanford* | 0 |
| Xba I *Xanthomonas badrii* | 1 |
| Xho I *Xanthomonas holicola* | 1 |
| Xma I *Xanthomonas marvacearum* | 1 |
| Xor II *Xanthomonas oryzae* | 0 | pAM 286
(a) Separation source: *Corynebacterium glutamicum* AJ11560 (FERM-P5485)
(b) Molecular weight: 3.0 mega dalton (calculated from a migration distance on electrophoresis in an agarose gel and the chain length of DNA under an electron microscope)
(c) Cleavage sites with restriction enzymes: Shown in Table 2.
(d) Map of cleavage sites with restriction enzymes: Shown in FIG. 2.
(e) Other properties: Cryptic plasmid

TABLE 2

| Restriction enzyme | Number of restriction Site |
| --- | --- |
| Alu I | ≧4 |
| Ava I | ≧2 |
| BamH I | 0 |
| Bcl I | 1 |
| Bgl II | 0 |
| BstE II | ≧4 |
| EcoR I | 0 |
| Hae II | 1 |
| HgiA I | ≧4 |
| Hind II | ≧4 |
| Hind III | 1 |
| Hpa II | ≧4 |
| Kpm I | 0 |
| Pvu II | 0 |
| Sac I | 0 |
| Sal I | 0 |
| Sau 3A | ≧4 |
| Sma I | 1 |
| Sst I | 0 |
| Xba I | 1 |
| Xho I | 1 |
| Xma I | 1 |
| Xor II | 0 |

Figure 3:
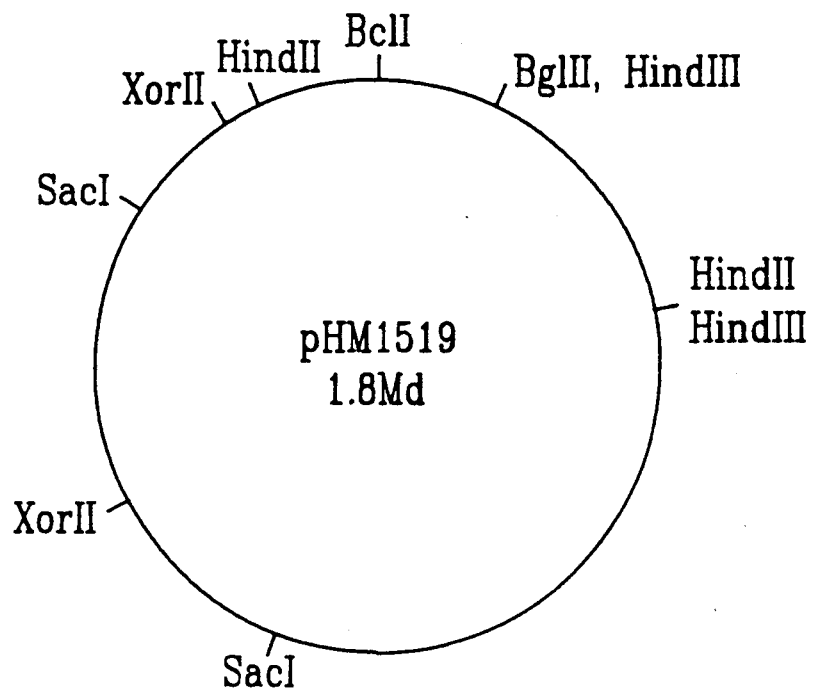
FIG. 3 shows a restriction map of plasmid pAM 1519.

(3) pHM 1519
(a) Separation source: *Corynebacterium glutamicum* ATCC 13058
(b) Molecular weight: 1.8 mega dalton
(c) Cleavage sites with restriction enzymes: Shown in Table 3.
(d) Map of cleavage sites with restriction enzymes: Shown in FIG. 3.
(e) Other property: Cryptic plasmid

TABLE 3

| Restriction enzyme | Number of restriction site |
| --- | --- |
| Ava I | ≧4 |
| BamH I | 0 |
| Bcl I | 1 |
| Bgl I | 1 |
| EcoR I | 1 |
| Hae II | ≧7 |
| HgiA I | ≧4 |
| Hind III | 2 |
| Kpn I | 0 |
| Sma I | 0 |
| Sac I | 2 |
| Xba I | 0 |
| Xho I | 0 |
| Xma I | 0 |

Figure 4:
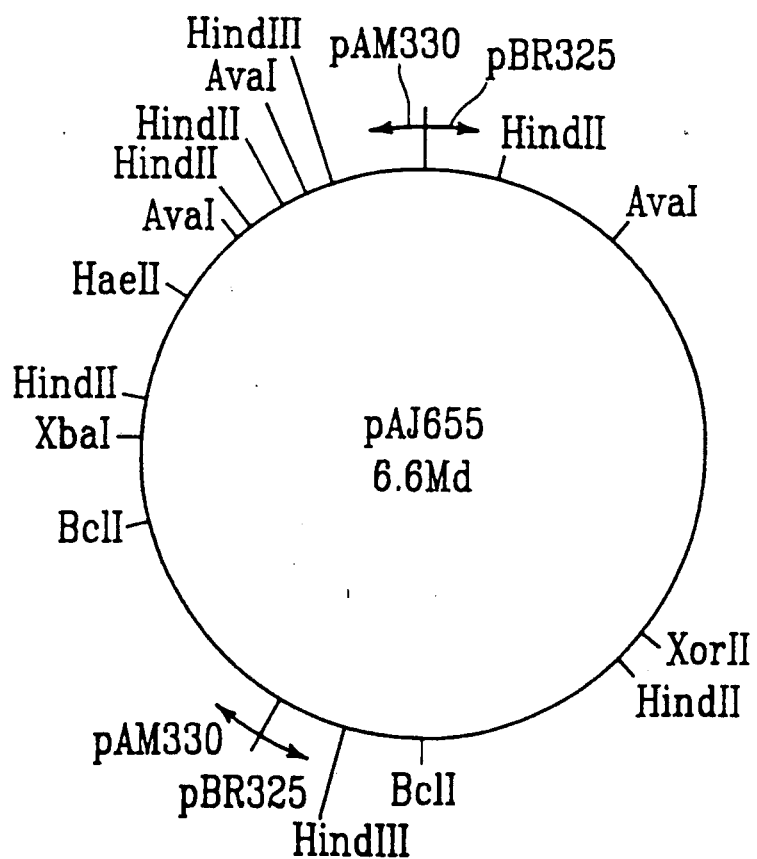
FIG. 4 shows a restriction map of composite plasmid pAJ 655.

(4) pAJ 655
(a) Host bacterium: *Escheriqhia coli* AJ 11882 (FERM-P6517=FERM-BP136, etc.)
(b) Molecular weight: 6.6 mega dalton
(c) Map of cleavage site with restriction enzymes: Shown in FIG. 4.
(d) Property: Composite plasmid of pAM 330 and pBR 325 (Gene, 4, 121 (1978)). It gives resistance to chloramphenicol.

Figure 5:
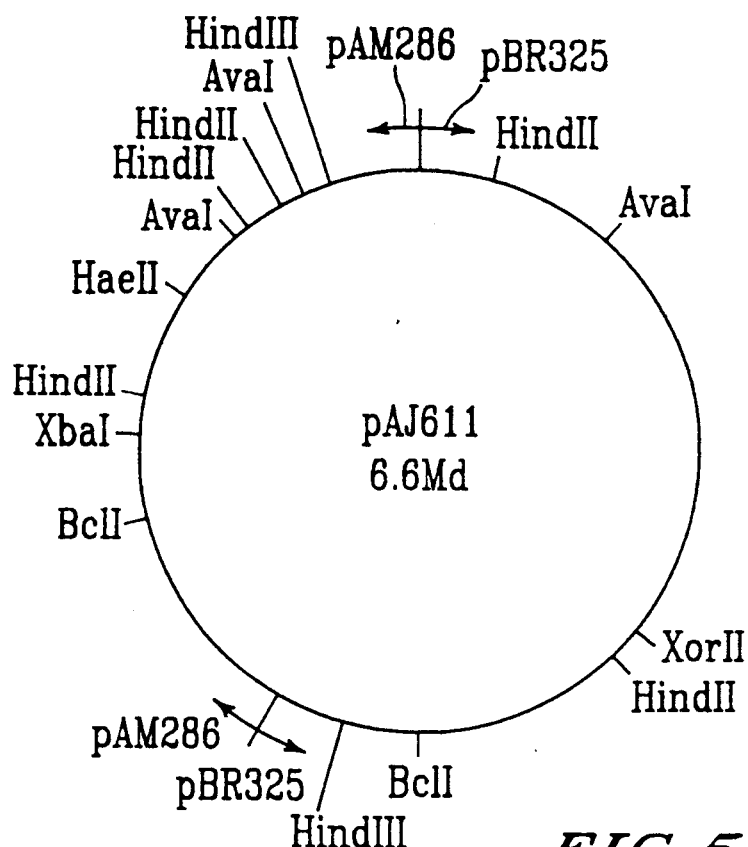
FIG. 5 shows a restriction map of composite plasmid pAJ 611.
Figure 6:
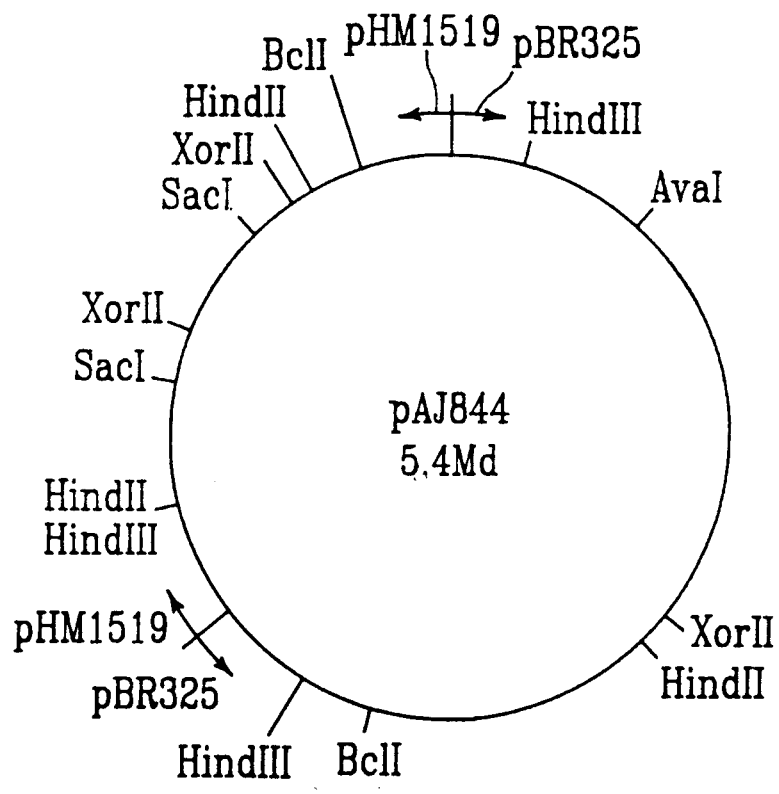
FIG. 6 shows a restriction map of composite plasmid pAJ 1844.

(5) pAJ 611
(a) Host bacterium: *Escherichia coli* AJ 11884 (FERM-P6519=FERM-BP138, etc.)
(b) Molecular weight: 6.6 mega dalton
(c) Map of cleavage site with restriction enzymes: Shown in FIG. 5.
(d) Property: Composite plasmid of pAM 286 and pBR 325 It gives resistance to chloramphenicol (6) pAJ 440
(a) Host bacterium: *Bacillus subtilus* AJ 111901 (FERM-BP140=ATCC 39139, etc.)
(b) Molecular weight: 6.0 mega dalton
(c) Map of cleavage site with restriction enzymes: Shown in FIG. 6.
(d) Property: Composite plasmid of pAM 330 and pUB 110 (J. Bacteriol., 134, 318 (1978)) It gives resistance to kanamycin.

Figure 7:
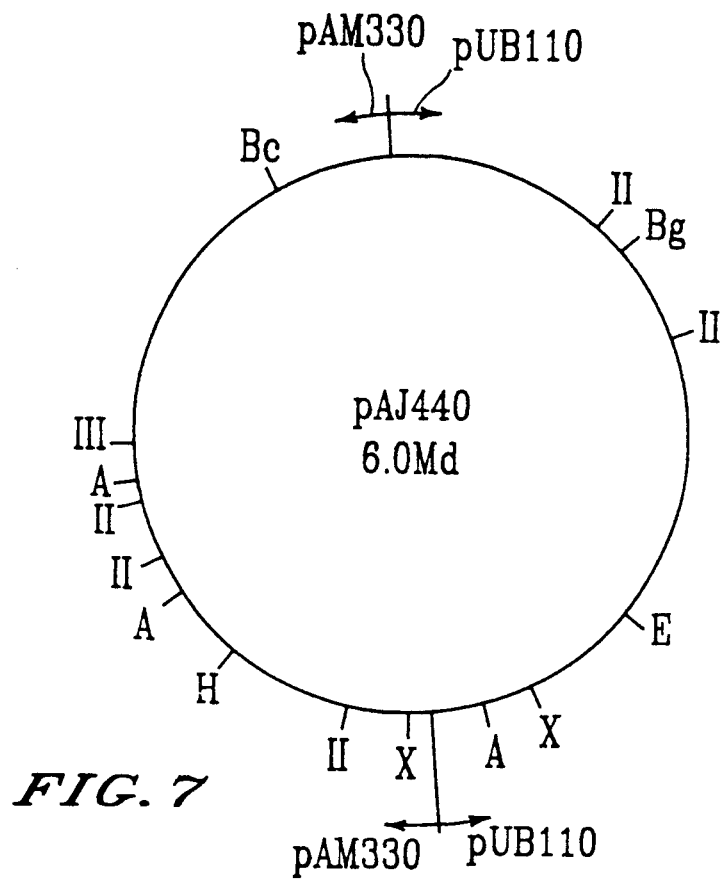
FIG. 7 shows a restriction map of composite plasmid pAJ 440.

(7) pAJ 1844
(a) Host bacterium: *Escherichia coli* AJ 11883 (FERM-P6519=FERM-BP137, etc.)
(b) Molecular weight: 5.4 mega dalton
(c) Map of cleavage site with restriction enzymes: Shown in FIG. 7.
(d) Property: Composite plasmid of pHM 1519 and pBR 325 It gives resistance to chloramphenicol.

Figure 8:
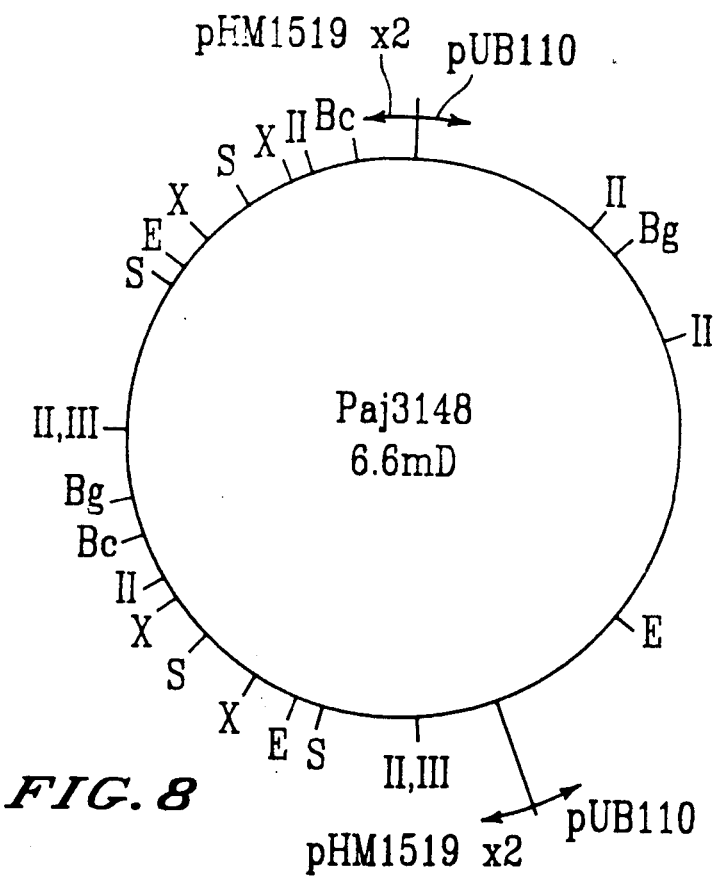
FIG. 8 shows a restriction map of composite plasmid pAJ 3148.

(8) pAJ 3148
(a) Host bacterium: *Corynebacterium glutamicum* SR 8203 ATCC 39137 etc.
(b) Molecular weight: 6.6 mega dalton
(c) Map of cleavage site with restriction enzymes: Shown in FIG. 8.
(d) Property: Composite plasmid of pHM 1519 and pUB 110 It gives resistance to kanamycin.

As other examples of such plasmids capable of self-replicating in cells of Coryneform glutamic acid-producing bacteria, there are pCG 1 (Japanese Patent Laid-Open No. 134500/1982), pCG 2 (Japanese Patent Laid-Open No. 35197/1983) and pCG 4 and pCG 11 (Japanese Patent Laid-Open No. 183799/1982), which will be all usable.

The chromosomal DNA and the vector DNA can be obtained by a usual method. The chromosomal DNA and vector DNA are each cut with a restriction enzyme. The cleavage of the vector DNA is achieved by cutting with a restriction enzyme that cuts the vector DNA at one place or by the partial digestion with a restriction enzyme that cuts the vector DNA at a plurality of sites. If reaction conditions are controlled so that cutting with a restriction endonuclease may be performed partially, many types of restriction enzymes can be used for the chromosome DNA.

For ligating the thus obtained chromosome DNA fragment with the thus cut vector DNA, an ordinary method using ligase can be used. On the other hand, there can be used also a method of adding deoxyadenylic acid and thymidilic acid or deoxyguanylic acid and deoxycytydylic acid to the chromosomal DNA fragment and cleaved vector DNA using a terminal transferase, respectively, and of mixing and then annealing the chromosome DNA fraction and the cleaved vector DNA both processed to ligate them with each other.

Incorporation of the thus obtained recombinant of the chromosome DNA with the vector plasmid into recipient belonging to Coryneform glutamic acid-producing bacteria can be carried out by treating cells with calcium chloride to increase the permeability of DNA as is reported regarding *Escherichia coli* K-12 (Mandel, M. and Higa, A., J. Mol. Biol., 53, 159, (1970)), or by incorporation at a specific growth stage when cells become capable of incorporating DNA into them (competent cells) as is reported regarding *Bacillus subtilis* (Duncan, C. H., Wilson, G. A. and Young, F. E., Gene, 1, 153 (1977)). In addition, it is also possible to incorporate plasmid into DNA-recipient by forming protoplasts or sphaeroplasts of the DNA-recipient which easily incorporate plasmid DNA, as is known relating to *Bacillus subtilis*, actinomyces, bacteria and yeasts (Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Acad. Sci. USA, 75, 1929 (1978)).

Although a high frequency of transformation can be obtained even with the above-mentioned method of *Bacillus subtilis*, the method of allowing the protoplast of microorganisms of the genus Corynebacterium: or Brevibacterium as stated in Japanese Patent Laid-Open No. 183799/1982 to incorporate DNA in the presence of polyethylene glycol or polyvinyl alcohol and of bivalent metallic ions can be also used for obtaining the high frequency. With a method for accelerating the incorporation of DNA by addition of carboxymethyl cellulose, dextran, "Ficoll" or "Pluronic" F68 (Selva Co.) instead of polyethylene glycol or polyvinyl alcohol, the same results can be obtained.

Selection of transformants obtained by ligating tryptophan biosynthesis genes with a vector plasmid and then incorporating the recombinant DNA into DNA-recipients can be easily achieved by selecting strains having lost nutritional requirement for tryptophan when strains requiring tryptophan are used as the recipients or by selecting strains having become resistant to tryptophan antagonists when tryptophan biosynthesis genes having resistance to tryptophan antagonists are incorporated into the recipients sensitive to tryptophan antagonists. Further, the selection of transformants can be also carried out using an increase in the productivity of tryptophan as a marker. If hereditary markers such as tolerance of drugs are present in vectors, the tolerance may be used for the easier selection of transformed strains together with the selection methods mentioned above.

A method for culturing the thus obtained L-tryptophan-producing bacteria does not specially differ from that for culturing conventional L-tryptophan-producing bacteria. Culture media used in the method are usual ones containing carbon sources, nitrogen sources, inorganic ions and, in addition, organic micronutrients such as amino acids and vitamins, if necessary. As carbon sources, there are used glucose, sucrose, lactose and the like and, in addition, those-containing starch hydrolyzed liquids, whey and molasses. As nitrogen source, ammonia gas, ammonia water, ammonium salts and others can be used.

The culture is carried out controlling the temperature and pH of culture medium under aerobic conditions until the production and accumulation of L-tryptophan stop.

Thus, a large amount of L-tryptophan is formed and accumulated in the culture liquid and a conventional method can be applied for recovering L-tryptophan from the culture liquid.

EXAMPLE (1) Preparation of chromosome DNA containing anthranilic acid phosphoribosyl transferase gene

*Brevibacterium lactofermentum* ATCC 13869 was inoculated into CMG culture medium (containing 1 g/dl of peptone, 1 g/dl of yeast extract, 0.5 g/dl of glucose and 0.5 g/dl of NaCl and having an adjusted pH value of 7.2) and was cultured at 30° C. for about 3 hours with shaking to collect the bacterial cells at the logarithmic phase of bacterial growth. After lysis of the bacterial cells with lysozyme.SDS, the chromosome DNA was extracted and purified by a conventional phenol-treatment method, and finally 3.5 mg of the DNA was obtained.

(2) Preparation of vector DNA

As a vector, pAJ 1844 (M.W. 5.4 mega dalton) was used and the DNA of pAJ 1844 was prepared by the following method.

First, *Brevibacterium lactofermentum* AJ 12037 containing pAJ 1844 as plasmid was inoculated into 100 ml of CMG culture medium and then cultured at 30° C. until the end part of the logarithmic phase of bacterial growth. After lysis of the bacterial cells by a lysozyme.SDS treatment, a supernatant clear liquid was obtained by centrifugation of 30,000×g for 30 minutes. After phenol-treatment of the liquid, DNA was precipitated and recovered by addition of two volumes of ethanol. The obtained DNA was dissolved in a small amount of TEN buffer (containing 20 mM of Tris HCl salt, 20 mM of NaCl and 1 mM of EDTA and having a pH value of 8.0) and then the DNA was separated by electrophoresis in an agarose gel. After that, the DNA was separated from the gel and thus about 15 μg of pAJ 1844 plasmid DNA was obtained.

(3) Insertion of chromosome DNA fragment into vector

Twenty microgram of chromosome DNA obtained in (1) and 10 microgram of plasmid DNA obtained in (2) were each treated at 37° C. for 1 hour with restriction endonuclease to cut them completely. After a heat-treatment at 65° C. for 10 minutes, the both reaction liquids were mixed with each other and in the mixed liquid the ligation reaction of DNA chains was carried out at 10° C. for 24 hours with DNA ligase derived from T4 phage in the presence of ATP and dithiothreitol. After a heat treatment at 65° C. for 5 minutes, two volumes of ethanol were added to the reaction liquid to precipitate and recover DNA after completion of the ligation reaction.

(4) Cloning of anthranilic acid phosphoribosyl transferase (PRT) gene

*Brevibacterium lactofermentum* T-13 (NRRLB-15347) deficient in PRT genes was used as the DNA-recipient. A protoplast transformation was used as the transformation method. First, the strains were cultured in 5 ml of CMG culture medium until the initial part of logarithmic phase of bacterial growth, and then, after addition of 0.6 unit/ml of penicillin, the strains were further cultured for 1.5 hours with shaking. The bacterial cells were collected by centrifugation and then washed with 0.5 ml of SMMP culture medium (pH 6.5) comprising 0.5 M of sucrose, 20 mM of maleic acid, 20 mM of magnesium chloride and 3.5% of "Pennassay" broth (Difco). Subsequently, the strains were suspended in SMMP culture medium containing 10 mg/ml of lysozyme at 30° C. for 20 hours to make them protoplast. After separation of the protoplast by centrifugation of 6000×g for 10 minutes, the protoplast was washed with SMMP and then it was again suspended in 0.5 ml of SMMP. The thus obtained protoplast and 10 microgram of DNA prepared in (3) were mixed with each other in the presence of 5 mM of EDTA, and then polyethylene glycol was added to the mixture in an amount of the final concentration of 30%. After that, the mixed liquid was let stand for 2 minutes at a room temperature to allow the DNA to be incorporated into the protoplast. After washing of the protoplast with 1 ml of SMMP culture medium, it was resuspended in 1 ml of SMMP culture medium and then it was cultured at 30° C. for 2 hours. The culture fluid was applied on a protoplast regeneration culture medium having a pH of 7.0. The protoplast regeneration culture medium contained 12 g of tris-(hydroxymethyl) aminomethane, 0.5 g of KCl, 10 g of glucose, 8.1 g of MgCl$_2$.6H$_2$O, 2.2 g of CaCl$_2$2H$_2$O, 4 g of peptone, 4 g of powder yeast extract, 1 g of "Casamino acid" (Difco Co.), 0.2 g of K$_2$HPO$_4$, 153 g of sodium succinate and 8 g of agar per 1 l of distilled water and 3 microgram/ml of chloramphenicol.

After cultivation of the protoplast on the regeneration culture medium at 30° C. for two weeks, about 10,000 colonies resistant to chloramphenicol appeared, and the colonies were inoculated onto a culture medium free from tryptophan (that is, -Trp culture medium containing 2% of glucose, 1% of ammonium sulfate, 0.25% of urea, 0.1% of potassium dihydrogenphosphate, 0.04% of MgSO$_4$.7H$_2$O, 2 ppm of iron ions, 2 ppm of manganese ions, 200 microgram/l of thiamin HCl salt, 50 microgram/l of biotin, 0.5% of "Casamino acid" and 1.8% of agar and having of pH value of 7.0) by a replica plating method. Thus, 22 strains, which are resistant to chloramphenicol and do not require for tryptophan, were obtained.

(5) Analysis of plasmid possessed by the transformed strains

By the same method as in (2), the lysate solution of the cells of the transformants was prepared, and then the plasmid DNA was separated from the solution by electrophoresis on an agarose gel. As a result of detection of plasmid DNA, plasmid larger than the vector pAJ 1844, was detected in three strains.

The representative strain of these strains was termed AJ 12029 (FERM-BP-275). When plasmid possessed by the strain AJ 12029 was cut with restriction enzyme PstI which had been used for the recombination of the gene, DNA fragments which were considered to contain PRT genes and had a molecular weight of about 1.3 mega dalton were detected.

(6) Re-transformation

For confirmation of the presence of PRT genes on the recombined plasmid containing 1.3 mega dalton DNA fragments detected in (5), *Brevibacterium lactofermentum* T-13 (NRRIB-15347) was again transformed with the plasmid DNA.

Of resulting colonies resistant to chloramphenicol, ten colonies were picked up and they were tested for tryptophan requirement. As the result, there were no colonies having the requirement, so that the presence of PRT genes or the above-mentioned recombined plasmid was verified.

(7) PRT activity of the transformed strain

The strains to be tested were cultured in 50 ml of CMG culture medium and a lysate was prepared from the cells by an ultrasonic treatment. The liquid was separated by centrifugation of 32,000×g for 30 minutes and a supernatant clear liquid was obtained. The PRT activity was measured using the supernatant clear liquid as a crude enzyme preparation and using an enzyme reaction preparation comprising 10 mM of Tris-HCl (pH 7.8), 5 μM of anthranilic acid, 0.25 mM of PRPP, 2 mM of magnesium chloride and 20% of glycerol. The reaction was carried out at 22° C. and the PRT activity was determined by measuring the decrease of anthranilic acid with a fluorophotometer (excitation 320 nm, measurement 395 nm). The results are shown in Table 4.

TABLE 4

| | Anthranilic acid phosphoribosyl transferase activity |
|---|---|
| | Anthranilic acid nmol/mg protein/min |
| T-13 | 0.02 |
| ATCC 13869 | 0.25 |
| AJ 12029 | 4.25 |

As shown in Table 4, the PRT activity was hardly observed with T-13 strains and it was clear that T-13 strains did not contain the above-mentioned enzyme. AJ 12029 which was a transformant obtained by incorporating recombined plasmid containing PRT genes into T-13 strains was observed to have about 17 times the PRT activity of the wild strain.

(8) Tryptophan productivity of the transformed strain

Recombined plasmid containing PRT genes was extracted from the above-mentioned AJ 12029 by the method of (2) and it was incorporated into *Brevibacterium lactofermentum* No. 9232 by the transformation method mentioned in (4). The resulting transformed strains were selected using resistance to chloramphenicol as a marker.

The thus obtained strains AJ 12020 (FERM-BP-276) and No. 9232 strains were cultured to test their tryptophan productivity. The results obtained are shown in Table 5.

A culture medium containing 100 g of glucose, 40 g of (NH$_4$)$_2$SO$_4$, 1 g of KH$_2$PO$_4$, 0.4 g of MgSO$_4$.7H$_2$O, 10 mg of FeSO$_4$.7H$_2$O, 10 mg of MnSO$_4$.4H$_2$O, 1 g of "Casamino acid", 300 microgram/l of biotin, 200 microgram/l of thiamine.HCl, 5 g of serine, 5 g of anthranilic acid and 50 g of CaCO$_3$ in 1 l of water and having a pH value of 7.0 was used for the culture. Each the strains was inoculated into 3 ml of the above-mentioned culture medium placed in a test tube and then cultured at 30° C. for 70 hours with shaking. L-tryptophan in the supernatant of the culture liquid obtained by centrifugation after the culture was determined by a liquid chromatography.

TABLE 5

| | Amount of tryptophan produced |
|---|---|
| | L-tryptophan |
| No. 9232 | <5 mg/dl |
| AJ 12020 | 76 mg/dl |

The above-mentioned No. 9232 is a revertant of a mutant derived from *Brevibacterium lactofermentum* ATCC 13869 and deficient in tryptophan synthetase. No. 9232 had tryptophan-productivity in an amount of 5 mg/dl and less while the tryptophan productivity of ATCC 13869 was not detected in the above-mentioned production culture medium. That was the reason No. 9232 was used for this experiment.

In order to obtain No. 9232 strains, it is possible to eliminate the composite plasmid in host cells without injuring the host cells. The plasmid may be lost spontaneously from the host cells and it can be also eliminated by a "curing" operation (Bact. Rev., 36, 361–405 (1972)).

An example of the "curing" operation is as follows. A small amount of the strain, that is, about 10$^4$ cells per ml are inoculated into a culture medium containing acridine orange in a concentration (2–50 mg/ml) for inhibiting incompletely the growth of the host, and then, after incomplete inhibition of the growth cf host, the strain is cultured at 27°–35° C. for one night (J. Bacteriol., 88, 261 (1964)). The culture fluid is applied on an agar culture medium and cultured at 27°–42° C. for one night. Most of colonies appearing on the culture medium have high possibilities of having no plasmid.

AJ 12037 is obtained by incorporating pAJ 1844 plasmid into ATCC 13869 by such a transformation method as stated in (4).

Plasmid pAJ 1844 used as a vector in the present invention is on deposit in the form of it having been incorporated into *Escherichia coli* AJ 11883 (that is, as FERM-P6519=FERM-BP137) in Fermentation Research Institute. Plasmid pAJ 1844 can be isolated and purified by the following method. AJ 11883 is, first, grown until the end part of logarithmic phase of bacterial growth and then, after lysis of cells with lysozyme and SDS, the lysate of cells is separated by centrifugation of 30,000×g to obtain a supernatant clear liquid, to which polyethyleneglycol is added to precipitate DNA. Subsequently, isolation of the DNA is carried out by an equilibrium density gradient centrifugation with cesium chloride-ethidium bromide.

What is claimed is:

1. A method for producing L-tryptophan, which comprises:
   culturing Coryneform glutamic acid-producing bacteria in a culture medium capable of producing L-tryptophan and then recovering the L-tryptophan accumulated in said culture medium,
   wherein said Coryneform glutamic acid-producing bacteria contain a plasmid capable of self-replicating cells of Coryneform glutamic acid-producing bacteria, said plasmid containing therein an antranilic acid phosphoribosyl transferase gene obtained from a Brevibacterium glutamic acid-producing bacteria.

2. The method according to claim 1, wherein said microorganism containing said plasmid is FERM-BP-275 or FERM-EP-276.

3. The method according to claim 1, wherein said microorganism is a Coryneform glutamic acid-producing bacteria resistant to a tryptophan antagonist.

4. The method according to claim 3, wherein said tryptophan antagonist is selected from the group consisting of 4-fluorotryptophan, 5-fluorotryptophan, 6-fluorotryptophan, 7-fluorotryptophan, 4-methyltryptophan, 5-methyltryptophan, 6-methyltryptophan, 7-methyltryptophan, napthylalanine, indoleacrylic acid, naphthylacrylic acid, β-(2-benzothienyl)-alanine, styrylacetic acid, indole ad tryptopzan.

5. A Coryneform glutamic acid-producing bacterium selected from the group consisting of FERM-BP-275 and FERM-BO-276.

* * * * *

UNITED STATES PATENT AND TRADEMARK OFFICE
CERTIFICATE OF CORRECTION

PATENT NO. : 5,034,318
DATED : JULY 23, 1991
INVENTOR(S) : KIYOSHI MIWA ET AL

It is certified that error appears in the above-identified patent and that said Letters Patent is hereby corrected as shown below:

Column 9, line 40, after "pH", insert --value--;
line 58, before "pH", delete "of", insert --a--.

Column 12, lines 26-27, after "self-replicating", insert --in--;
line 34, delete "FERM-EP-276", insert --FERM-BP-276--;
line 48, delete "FERM-BO-276", insert --FERM-BP-276--.

Signed and Sealed this

Ninth Day of November, 1993

*Attest:*

*Attesting Officer*

BRUCE LEHMAN

*Commissioner of Patents and Trademarks*